(12) United States Patent
Liang et al.

(10) Patent No.: US 11,421,214 B2
(45) Date of Patent: Aug. 23, 2022

(54) SYSTEM BASED ON A NEW NITRILE HYDRATASE FOR HIGHLY EFFICIENT CATALYTIC HYDRATION REACTION OF ALIPHATIC DINITRILES

(71) Applicant: DALIAN UNIVERSITY OF TECHNOLOGY, Liaoning (CN)

(72) Inventors: Changhai Liang, Liaoning (CN); Li Wang, Liaoning (CN); Shengxian Liu, Liaoning (CN); Tongyi Dou, Liaoning (CN); Changhao Cui, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 289 days.

(21) Appl. No.: 16/772,063

(22) PCT Filed: Oct. 25, 2019

(86) PCT No.: PCT/CN2019/113301
§ 371 (c)(1),
(2) Date: Jun. 11, 2020

(87) PCT Pub. No.: WO2020/155690
PCT Pub. Date: Aug. 6, 2020

(65) Prior Publication Data
US 2021/0087547 A1  Mar. 25, 2021

(30) Foreign Application Priority Data
Jan. 31, 2019 (CN) .......................... 201910098275.6

(51) Int. Cl.
*C12N 1/20* (2006.01)
*C12N 9/88* (2006.01)
(Continued)

(52) U.S. Cl.
CPC ................. *C12N 9/88* (2013.01); *C12N 1/20* (2013.01); *C12N 15/74* (2013.01); *C12P 13/02* (2013.01); *C12Y 402/01084* (2013.01)

(58) Field of Classification Search
None
See application file for complete search history.

(56) References Cited

U.S. PATENT DOCUMENTS

| 10,655,152 | B2 * | 5/2020 | Budde | ....................... C12N 9/78 |
| 2017/0283840 | A1 * | 10/2017 | Braun | .................. D21H 17/375 |

(Continued)

FOREIGN PATENT DOCUMENTS

| CN | 101619299 A | 1/2010 | |
| CN | 109797164 A | 5/2019 | |
| WO | WO-2004067738 A2 * | 8/2004 | ............... C12N 9/88 |

OTHER PUBLICATIONS

Rucka, L., et al., "Expression control of nitrile hydratase and amidase genes in Rhodococcus erythropolis and substrate specificities of the enzymes" Antonie van Leeuwenhoek, Apr. 30, 2014, pp. 1179-1190, vol. 105.

(Continued)

*Primary Examiner* — Richard C Ekstrom
(74) *Attorney, Agent, or Firm* — Muncy, Geissler, Olds & Lowe, P.C.

(57) ABSTRACT

The invention belongs to the technical field of green chemistry, and provides a novel system based on a new nitrile hydratase for highly efficient catalytic conversion of aliphatic dinitriles. The invention discloses a new application of nitrile hydratase using *Rhodococcus erythropolis* CCM 2595 in catalyzing aliphatic dinitrile. In particular, the enzyme can regioselectivity catalyze the formation of 5-cyanopyramides from adiponitrile with high reaction rate under (Continued)

mild reaction conditions, which provides a new method for the industrial production of 5-cyanopyramides.

3 Claims, 4 Drawing Sheets

Specification includes a Sequence Listing.

(51) Int. Cl.
  *C12P 13/02* (2006.01)
  *C12N 15/74* (2006.01)

(56) References Cited

U.S. PATENT DOCUMENTS

2019/0112399 A1\* 4/2019 Langlotz ................. C08F 20/56
2021/0087547 A1\* 3/2021 Liang ....................... C12N 9/88

OTHER PUBLICATIONS

Kubac, D., et al., "Biotransformation of nitriles to amides using soluble and immobilized nitrile hydratase from Rhodococcus erythropolis A4" Journal of Molecular Catalysis B: Enzymatic, Sep. 11, 2007, pp. 107-113, vol. 11.9.

Kamble, L., et al., "Nitrile hydratase of Rhodococcus erythropolis: characterization of the enzyme and the use of whole cells for biotransformation of nitriles" 3 Biotech, Dec. 16, 2012, pp. 319-330, vol. (2013) 3:319-330.

Moreau, J.L., et al., "Application of High-performance liquid chromatography to the study of the biological transformation of Adiponitrile by Nitrile Hydratase and Anlidase" Analyst, Dec. 31, 1991, pp. 1381-1383, vol. 116.

Strnad, H., et al., "Genome sequence of Rhodococcus erythropolis strain CCM2595, a phenol derivative-degrading bacterium" Genome Announcements, Mar. 20, 2014, pp. 1-2, vol. 2—Issue 2.

Cejkova, A, et al., "Potential of Rhodococcus erythropolis as a bioremediation organism" World Journal of Microbiology & Biotechnology, Dec. 31, 2005, pp. 317-321, vol. 21.

\* cited by examiner

```
                     SEQUENCE LISTING

<160> NUMBER OF SEQ ID NOS: 1

<210> SEQ ID NO 1
<211> LENGTH: 2596
<212> TYPE: DNA
<213> ORGANISM: Rhodococcus erythropolis

<400> SEQUENCE: 1
catatgtcag taacgatcga ccacacaacg gagaacgccg caccggccca ggcgccggtc      60
tccgatcgcg cgtgggccct gttccgcgca ctcgacggta agggattggt acccgacggt     120
tacgtcgagg gatggaagaa gaccttcgag gaggacttca gtccaaggcg cggagcggaa     180
ttggtcgcgc gggcttggac cgaccccgat ttccggcaac tgcttctcac cgacggtacc     240
gccgcggttg cccagtacgg atatctgggc ccccagggcg aatacatcgt ggcagtcgaa     300
gacaccccga ccctcaagaa cgtgatcgtg tgctcgctgt gttcatgcac cgcgtggccc     360
atcctcggtc tgccgccgac ctggtacaag agtttcgaat accgtgcacg cgtggtccgc     420
gagccacgga aggttctctc cgagatggga accgagatcg cgtcggacgt cgagatccgc     480
gtctacgaca ccaccgccga aactcggtac atggtcctac cgcaacgtcc cgcaggcacc     540
gaaggctgga gccaggaaca actgcaggaa atcgtcacca aggactgcct gatcggcgtc     600
gcagtcccgc aggtccccac cgtctgacca ccccgacaag aaagaagcac accatggatg     660
gagtacacga tcttgccgga gttcaaggct tcggcaaagt cccgcatacc gtcaacgccg     720
acatcggccc caccttccac gccgagtggg aacacctgcc gtacagcctg atgttcgccg     780
gtgtcgccga actcggggcc ttcagcgtcg acgaagttcg atacgtcgtc gagcggatgg     840
agccccgcca ctacatgatg accccgtact acgagcggta cgtcatcggc gtcgcggcgc     900
tgatggtcga aaagggaatc ctgacgcagg aagagctcga aagccttgca ggaggaccgt     960
tcccactctc acggccaagc gaatccgaag gccgaccggc tcgcgtcgac acaaccacct    1020
tcgaggtcgg tcagcgagta cgtgtgcgag acgaatacgt tcccgggcat attcgaatgc    1080
ctgcttactg ccgaggacgg gtggggacca tcgctcaccg gaccaccgag aagtggccgt    1140
tccccgacgc aatcggtcac ggccgcaacg acgccggcga agaacccacc taccacgtga    1200
cgttcgctgc ggaggaattg ttcggcagcg acaccgacgg cggaagcgtc gttgtcgacc    1260
tcttcgaggg ttacctcgag cctgcggcct gatcttccag cattccaggc ggcggtcacg    1320
cgatcgcagc ggttcgcgtg accgccgcct gatcacaacg attcactcat tcggaaggac    1380
actggaaatc atggtcgaca cacgacttcc ggtcacggtg ctgtcaggtt tcctgggcgc    1440
```

```
cgggaagacg acgctactca acgagatcct gcgcaatcgg gagggccgcc gggttgcggt    1500
gatcgtcaac gacatgagcg aaatcaacat cgacagtgca gaagtcgagc gtgagatctc    1560
gctcagtcgc tccgaggaga aactggtcga gatgaccaac ggctgcatct gctgcactct    1620
gcgagaggat cttctttccg agataagcgc cttggccgcc gatggccgat tcgactacct    1680
tctcatcgaa tcttcgggca tctccgaacc gctgcccgtc gcggagacgt tcaccttcat    1740
cgataccgac ggccatgccc tggccgacgt cgcccgactc gacaccatgg tcacagtcgt    1800
cgacggcaac agttttctgc gcgactacac ggctggaggt cgcgtcgaag ccgatgcccc    1860
ggaagatgaa cgcgacatcg cggatctgct tgtcgatcag atcgagtttg ccgacgtcat    1920
cctggtgagc aaggccgatc tcgtctcgca ccagcacctg gtcgaattga cttcggtcct    1980
aagatctttg aacgcaactg ctgcgatagt tccgatgact ctcggccgta tcccactcga    2040
cacgattctc gataccggct tgttctcgct cgagaaagct gctcaggccc ctggatggct    2100
acaagaactc caaggtgaac acaccccga aaccgaggag tacggaatcg gttcggtggt    2160
gtaccgcgag cgcgcgccct tccacccaca acgcctgcat gatttcctga gcagcgagtg    2220
gaccaacgga aagttacttc gggccaaggg ctactactgg aatgccggcc ggttcaccga    2280
gatcgggagt atttctcagg ccggtcatct cattcgccac ggatacgtcg gccgttggtg    2340
gaagtttcta ccccgtgacg agtggccggc cgacgactac cgtcgcgacg aatcctcga    2400 caagtgggaa gaacctgtcg gtgactgccg acaagaactc gtcttcatcg gccaatccat    2460
cgacccatct cgactgcacc gagaactcga cgcgtgtcta ctcaccacag ccgagatcga    2520
actcgggcca gacgtgtgga ccacctggag cgaccccctg ggcgtcggct ataccgacca    2580
gaccgtttga aagctt                                                    2596
```

SYSTEM BASED ON A NEW NITRILE HYDRATASE FOR HIGHLY EFFICIENT CATALYTIC HYDRATION REACTION OF ALIPHATIC DINITRILES

TECHNICAL FIELD

The invention belongs to the technical field of green chemistry, which involves the application of nitrile hydratase derived from the *Rhodococcus erythropolis* CCM2595 in the regioselective catalytic reaction of aliphatic dinitrile to cyanamide.

BACKGROUND

Nitrile hydratase (EC 4.2.1.84, NHase) is a class of metal enzymes in nitrile metabolism that can catalyze nitriles to amides by hydration. NHase catalyzes nitrile substances to acrylamide, nicotinamide, 5-cyanglutamide, etc. It is widely used in the production of fine chemicals, especially pesticides and organic solvents. Nitrile compounds are produced mainly through the sewage discharge from chemical factory, from herbicide or as accidental leakage into people's lives. Most of the nitriles have neurotoxicity, which are also carcinogenic or teratogenic to human or animals. Therefore, NHase plays an important role in environmental protection, as they can degrade nitrile compounds.

5-cyanovaleramide (5-CVAM) can be used for the synthesis of azafenidin and 6-aminocaproic amide, Azafenidin can be used as herbicides with high potency, low toxicity and no long-term adverse effects on the environment. 6-aminocaproic amide is an important intermediate for the synthesis of caprolactam, which is an important chemical raw material. 5-CVAM can be prepared by chemical catalytic or biocatalytic hydration of adiponitrile. Adiponitrile contains two cyanogroups, the catalytic reaction requires the regioselective hydration of one of the cyanogroups to form 5-CVAM. Compared with the harsh chemical reaction conditions such as high temperature, high pressure and the use of copper catalyst, and the production of a lot of byproducts, biocatalysis has the advantages of to accelerate reaction under mild conditions, high specificity, high regioselectivity, economic feasible and environmental benign.

According to the authoritative database BRENDA which have the data of the latest biocatalytic enzymes, only *Pseudomonas* was found to catalyze adiponitrile to 5-CVAM with high regioselectivity. Therefore, it is necessary to find new nitrile hydratase which can be used in the rapid and efficient production of 5-CVAM in the chemical industry.

*Rhodococcus erythropolis* CCM2595 used in the present invention belongs to *Rhodococcus*, which was shown to degrade specifically phenol, hydroxybenzoate, p-chlorophenol, aniline and other aromatic compounds by far [Strnad H, Patek M, Fousek J, Szokol J, Ulbrich P, Nesvera J, Paces V, Vlcek C: Genome Sequence of *Rhodococcus erythropolis* Strain CCM2595, a Phenol Derivative-Degrading Bacterium. Genome announcements 2014, 2(2)]. There is no report on the biocatalytic reaction of *Rhodococcus erythropolis* CCM2595 to nitrile hydration of aliphatic dinitriles until now.

SUMMARY

The invention provides an application of NHase derived from the *Rhodococcus erythropolis* CCM2595 for the production of cyanamide from aliphatic dinitriles.

The Technical Solution of the Invention

A novel system based on a new nitrile hydratase for highly efficient catalytic hydration reaction of aliphatic dinitriles, in which the concentration of recombinant bacteria with nitrile hydratase is 1-3 g/L, the concentration of aliphatic dinitriles is 20-50 mM/L, conversion system comprises phosphate buffer saline solution with pH=7-8, temperature of 25° C., and oscillation with 200 revolutions per minute (rpm) for reaction. The reaction is quenched by adding equal volume of methanol after 5 min of cultivation. Then supernatant is collected after centrifugation. After filtering the supernatant for high performance liquid chromatography detection, the regioselectivity of the recombinant bacteria with nitrile hydratase towards aliphatic dinitriles is more than 90%.

The steps are as follows:

(1) Plasmid construction:

The nucleotides sequence of nitrile hydratase derived from *Rhodococcus erythropolis* CCM2595 is shown as follows:

```
  1   CATATGTCAG TAACGATCGA CCACACAACG GAGAACGCCG CACCGGCCCA
 51   GGCGCCGGTC TCCGATCGCG CGTGGGCCCT GTTCCGCGCA CTCGACGGTA
101   AGGGATTGGT ACCCGACGGT TACGTCGAGG GATGGAAGAA GACCTTCGAG
151   GAGGACTTCA GTCCAAGGCG CGGAGCGGAA TTGGTCGCGC GGGCTTGGAC
201   CGACCCCGAT TTCCGGCAAC TGCTTCTCAC CGACGGTACC GCCGCGGTTG
251   CCCAGTACGG ATATCTGGGC CCCCAGGGCG AATACATCGT GGCAGTCGAA
301   GACACCCCGA CCCTCAAGAA CGTGATCGTG TGCTCGCTGT GTTCATGCAC
351   CGCGTGGCCC ATCCTCGGTC TGCCGCCGAC CTGGTACAAG AGTTTCGAAT
401   ACCGTGCACG CGTGGTCCGC GAGCCACGGA AGGTTCTCTC CGAGATGGGA
451   ACCGAGATCG CGTCGGACGT CGAGATCCGC GTCTACGACA CCACCGCCGA
501   AACTCGGTAC ATCGTCCTAC CGCAACGTCC CGCAGGCACC GAAGGCTGGA
551   GCCAGGAACA ACTGCAGGAA ATCGTCACCA AGGACTGCCT GATCGGCGTC
601   GCAGTCCCGC AGGTCCCCAC CGTCTGACCA CCCCGACAAG AAAGAAGCAC
```

-continued

```
 651   ACCATGGATG GAGTACACGA TCTTGCCGGA GTTCAAGGCT TCGGCAAAGT
 701   CCCGCATACC GTCAACGCCG ACATCGGCCC CACCTTCCAC GCCGAGTGGG
 751   AACACCTGCC GTACAGCCTG ATGTTCGCCG GTGTCGCCGA ACTCGGGGCC
 801   TTCAGCGTCG ACGAAGTTCG ATACGTCGTC GAGCGGATGG AGCCCCGCCA
 851   CTACATGATG ACCCCGTACT ACGAGCGGTA CGTCATCGGC GTCGCGGCGC
 901   TGATGGTCGA AAAGGGAATC CTGACGCAGG AAGAGCTCGA AAGCCTTGCA
 951   GGAGGACCGT TCCCACTCTC ACGGCCAAGC GAATCCGAAG CCCGACCGGC
1001   TCGCGTCGAC ACAACCACCT TCGAGGTCGG TCAGCGAGTA CGTGTGCGAG
1051   ACGAATACGT TCCCGGGCAT ATTCGAATGC CTGCTTACTG CCGAGGACGG
1101   GTGGGGACCA TCGCTCACCG GACCACCGAG AAGTGGCCGT TCCCCGACGC
1151   AATCGGTCAC GGCCGCAACG ACGCCGGCGA AGAACCCACC TACCACGTGA
1201   CGTTCGCTGC GGAGGAATTG TTCGGCAGCG ACACCGACGG CGGAAGCGTC
1251   GTTGTCGACC TCTTCGAGGG TTACCTCGAG CCTGCGCCCT GATCTTCCAG
1301   CATTCCAGGC GGCGGTCACG CGATCGCAGC GGTTCGCGTG ACCGCCGCCT
1351   GATCACAACG ATTCACTCAT TCGGAAGGAC ACTGGAAATC ATGGTCGACA
1401   CACGACTTCC GGTCACGGTG CTGTCAGGTT CCTGGGCGC CGGGAAGACG
1451   ACGCTACTCA ACGAGATCCT GCGCAATCGG GAGGGCCGCC GGGTTGCGGT
1501   GATCGTCAAC GACATGAGCG AAATCAACAT CGACAGTGCA GAAGTCGAGC
1551   GTGAGATCTC GCTCAGTCGC TCCGAGGAGA AACTGGTCGA GATGACCAAC
1601   GGCTGCATCT GCTGCACTCT GCGAGAGGAT CTTCTTTCCG AGATAAGCGC
1651   CTTGGCCGCC GATGGCCGAT TCGACTACCT TCTCATCGAA TCTTCGGGCA
1701   TCTCCGAACC GCTGCCCGTC GCGGAGACGT TCACCTTCAT CGATACCGAC
1751   GGCCATGCCC TGGCCGACGT CGCCCGACTC GACACCATGG TCACAGTCGT
1801   CGACGGCAAC AGTTTTCTGC GCGACTACAC GGCTGGAGGT CGCGTCGAAG
1851   CCGATGCCCC GGAAGATGAA CGCGACATCG CGGATCTGCT TGTCGATCAG
1901   ATCGAGTTTG CCGACGTCAT CCTGGTGAGC AAGGCCGATC TCGTCTCGCA
1951   CCAGCACCTG GTCGAATTGA CTTCGGTCCT AAGATCTTTG AACGCAACTG
2001   CTGCGATAGT TCCGATGACT CTCGGCCGTA TCCCACTCGA CACGATTCTC
2051   GATACCGGCT TGTTCTCGCT CGAGAAAGCT GCTCAGGCCC TGGATGGCT
2101   ACAAGAACTC CAAGGTGAAC ACACCCCCGA AACCGAGGAG TACGGAATCG
2151   GTTCGGTGGT GTACCGCGAG CGCGCGCCCT TCCACCCACA ACGCCTGCAT
2201   GATTTCCTGA GCAGCGAGTG GACCAACGGA AAGTTACTTC GGGCCAAGGG
2251   CTACTACTGG AATGCCGGCC GGTTCACCGA GATCGGGAGT ATTTCTCAGG
2301   CCGGTCATCT CATTCGCCAC GGATACGTCG GCCGTTGGTG GAAGTTTCTA
2351   CCCCGTGACG AGTGGCCGGC CGACGACTAC CGTCGCGACG GAATCCTCGA
2401   CAAGTGGGAA GAACCTGTCG GTGACTGCCG ACAAGAACTC GTCTTCATCG
2451   GCCAATCCAT CGACCCATCT CGACTGCACC GAGAACTCGA CGCGTGTCTA
2501   CTCACCACAG CCGAGATCGA ACTCGGGCCA GACGTGTGGA CCACCTGGAG
2551   CGACCCCCTG GGCGTCGGCT ATACCGACCA GACCGTTTGA AAGCTT
```

The sequence contains 2596 nucleotides, plasmid pET-24a (+) is used as the expression vector. According to the characteristics of restriction sites of the plasmid, NdeI and Hind III are selected as restriction site to insert the nitrile hydratase gene which is obtained by polymerase chain reaction (PCR). After digestion, the corresponding DNA fragment is recovered and purified, and is inserted into the kanamycin KanR resistance gene fragment. The T7 terminator is transformed into *E. coli* Top 10, the recombinant plasmid is obtained, conformed with digestion and named G0130349-1.

(2) Protein expression verification: The recombinant plasmid obtained in step (1) is transformed into two competent *E. coli*, BL21(DE3) and Arctic Expression (DE3) respectively before adding to LB liquid medium for culture and expansion, then the obtained bacterial solution is coated on LB solid plate containing 50 μg/ml kanamycin (kart) before inverted culture at 37° C. for 24 h. The monoclone on the plate is selected and planted in LB liquid medium. When OD value reaches 0.6-0.8 after culturing, 0.1-1 mM/L Isopropylthiogalactoside (IPTG) is then added as inducer for 3-24 h. After the induction, the bacteria are collected by centrifugation. The bacteria are broken by ultrasonic after washing with PBS. SDS-PAGE analysis is carried out to verify the protein expression of nitrile hydratase.

(3) Preparation of bacterial solution: the monoclone picked from Arctic Expression (DE3) plate in step (2) is inoculate to LB liquid medium which contains 50 μg/ml Kan. Seed solution is obtained and collected after shake cultivation at 37° C., at 220 rpm for 12-18 h. The seed solution is then inoculated into LB liquid medium containing 50 μg/ml Kan with volume ratio of 1%. When OD value reaches 0.6-0.8 after shake cultivation at 37° C., IPTG is added to reach the final concentration of 0.1 inti/L. After continuous shake cultivation at 16° C., at 220 rpm for 24 h, fermentation broth is collected. The recombinant bacteria are collected by centrifugation, washed with PBS buffer (pH=7-8) for 2-3 times and resuspend for use in next experiment.

(4) The catalytic reaction of aliphatic dinitriles: The concentration of the recombinant bacteria is 1-3 g/L. The concentration of the aliphatic dinitriles is 20-50 mMYL. The conversion system comprises phosphate buffer saline solution with pH=7-8, at temperature of 25° C., and oscillating rate of 200 rpm. The reaction is quenched by adding equal volume of methanol after 5 min-24 h cultivation. The supernatant is collected after centrifugation. The supernatant is filtered for high performance liquid chromatography detection.

The invention has the following beneficial effects: The invention provides a new application of nitrile hydratase derived from *Rhodococcus erythropolis* CCM2595 in the catalytic reaction of aliphatic dinitriles.

DETAILED DESCRIPTION

The specific embodiments of the present invention are further described below in conjunction with the drawings and technical solutions.

Embodiment 1: Expression Validation of the ReNHase

Figure 1:
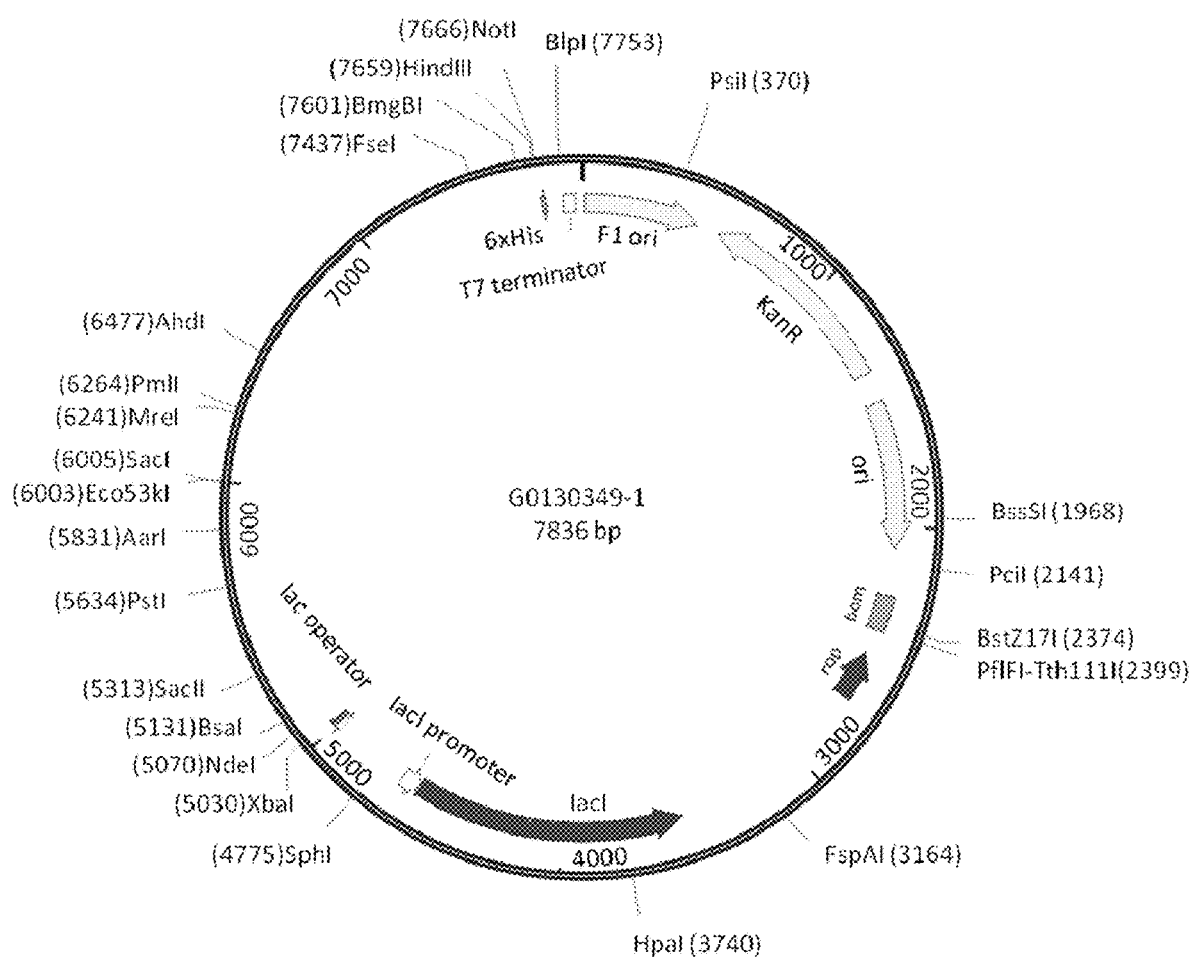
FIG. 1: Map of ReNHase (nitrile hydratase from *R. erythropolis*) gene in Plasmid vector pET-24a (±)
Figure 2:
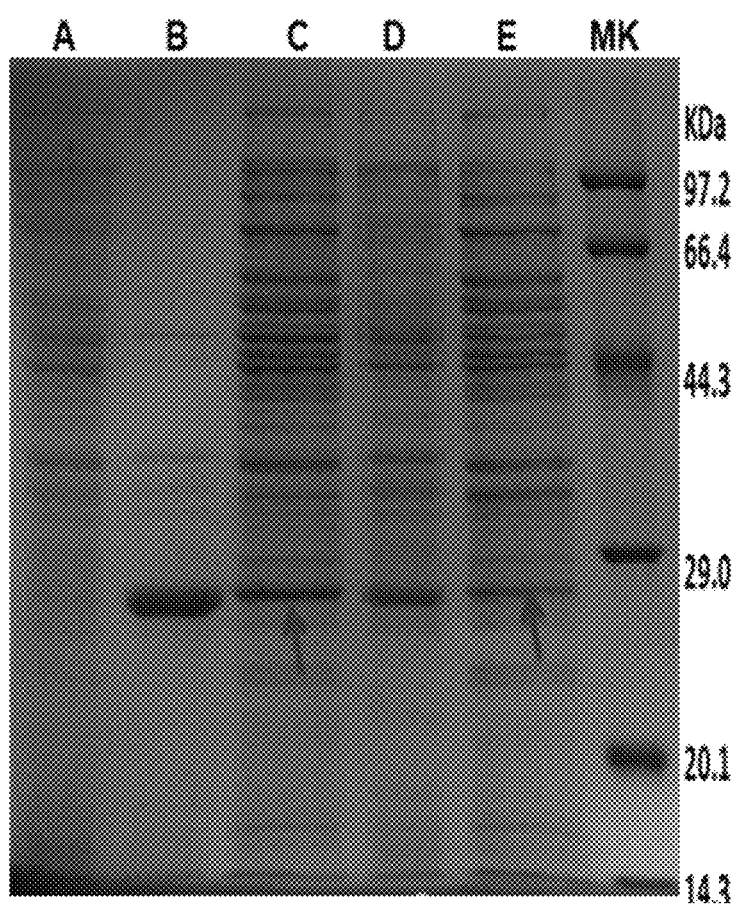
FIG. 2: Expression of the ReNHase from recombinant *E. coli* by the SDS-PAGE.
Lane A: Negative control;
Lane B: 37° C. temperature induced fragmentation (BL21 (DE3));
Lane C: 37° C. temperature induced disrupted supernatant (BL21(DE3));
Lane D: 1.6° C. temperature induced fragmentation (Arctic Express (DE3));
Lane E: 16° C. temperature induced disrupted supernatant (Arctic Express (DE3)).

1 μl plasmid was added to 100 μl BL21. (DE3) and Arctic expression (DE3) competent *E. coli* respectively. After placed in ice bath for 20 min, it was heated and shocked at 42° C. for 90 sec. It was then put into ice quickly for 3 min, then 600 μl LB liquid culture medium was added, and it was vibrated at 37° C. and at 220 rpm for 1 h. 200 μl bacterial solution was taken and coated on the LB plate containing 50 μg/ml Kan, and finally carried out inverted culture at 37° C. for 24 h. On the next day, two colonies of BL21 (DE3) and one clone of Arctic expression (DE3) were inoculated into the 4 ml shaker tube with LB culture medium containing 50 μg/ml Kan respectively. It was cultured under the condition of 37° C. and 220 rpm until the OD value was about 0.6. One tube of BL21 (DE3) without IPTG was used as negative control, one another tube with IPTG to the final concentration of 1 mMIL was induced at 37° C. for 3 h, IPTG was added to the single tube of Arctic expression (DE3) until the final concentration reached 0.1 mM/1, then it was induced at 16° C. for 24 h. On the next day, the supernatant was centrifuged at 12000 rpm for 1 min to collect the bacteria, and the buffer solution (20 mkt PB, 150 mM NaCl, pH7.4) was added, then the bacteria was crushed at 300 W power for 4 S, with an interval of 6 s. The bacteria were broken for a total of 30 cycles. SDS-PAGE analysis was carried out. 12% separation gel and 5% concentration gel were selected. The electrophoresis conditions were 80 V for 20 min and then 160 V for 100 min. As shown in FIG. 2, the target protein subunit (about 27 kDa) was expressed successfully in the supernatant.

Embodiment 2: The Reaction of Adiponitrile Catalyzed by ReNHase (1) Seed culture: a monoclone of Arctic expression (DE3) was selected and inoculated in a shaker tube with 4 ml LB culture medium containing 50 μg/ml Kan, and was shaken at 37° C. and at 220 rpm for 24 h.

(2) Induction culture: 2 ml bacterial solution in a flask containing 200 ml LB culture solution and 50 μg/ml Kan was inoculated, shaken at 37° C., at 220 rpm for about 3 h until the OD value reached 0.6-0.8, then IPTG was added to reach its final concentration of 0.1 mM/L, and finally it was incubated at 16° C., at 220 rpm for 24 h.

(3) Bacteria collection: the solution was centrifuged at 3000 rpm for 10 min. The supernatant was discarded, washed twice with PBS buffer of pH=7.4, and resuspended the bacteria with 10 ml PBS buffer.

Figure 3:
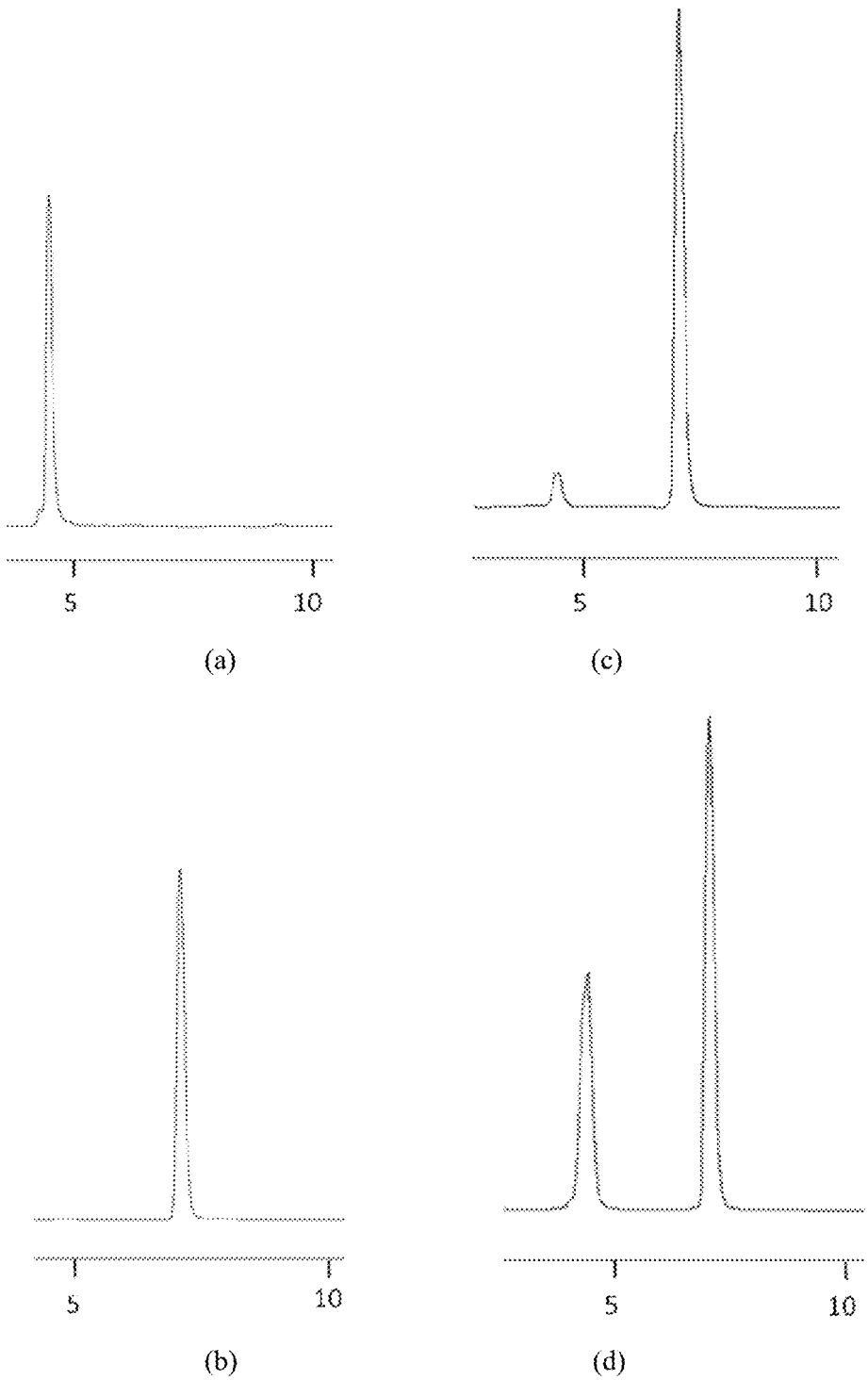
FIG. 3: The HPLC analysis results of substrate and products.
(a) standard sample-adipamide;
(b) standard sample-5-CVAM;
(c) The products of catalytic reaction of adiponitrile by ReNHase after 5 min;
(d) The products of catalytic reaction of adiponitrile by ReNHase in after 30 min.

(4) High performance liquid chromatography detection: 150 μl resuspended bacteria was added to 300 μl PBS buffer, then 50 μl 200 mM adiponitrile was added, and reacted at 25° C.; 200 rpm. The reaction time was 5 min, 10 min, 15 min, 30 min, 1 h, 2 h, 3 h, 6 h, 15 h, 24 h, respectively. After the reaction, 500 μl methanol was added to quench the reaction. The supernatant was collected after centrifuged at 10 min, 13000 rpm; then filtered by 0.22 μm strainer for HPLC detection. HPLC detection method: Ultimate 5 μm 4.6×250 min LP-C18 column was used, and the following solvent system was 25 mM $H_3PO4$ buffer and methanol (89:11, vol:vol); detection wavelength was 200 ran, column temperature was 25° C., flow rate was 1 ml/min. As shown in FIG. 3, (a) the peak time of standard sample adipamide was 4.4 min; (b) the peak time of standard sample 5-CVAM was 7.1 min; (c) The conversion rate of adiponitrile was 100% and the regioselectivity of 5-CVAM was more than 90% when the reaction was carried out for 5 min. following step (4) of experiment 2. (d) With the increase of reaction time, the production of 5-CVAM decreased, the production of adipamide increased, indicating that the nitrile hydratase catalyze adiponitrile with step reaction.

Figure 4:
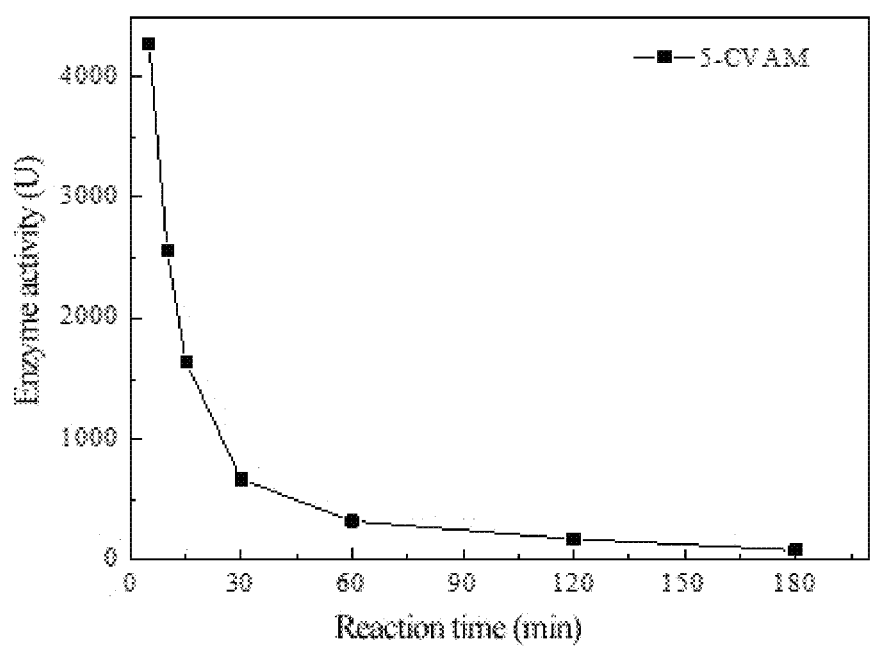
FIG. 4: Curve of enzymatic activity of product 5-CVAM with time.

As shown in FIG. 4, when the final concentration of adiponitrile was 50 mM, the product 5-CVAM with the primary total enzyme activity could reach 4269 U. With the increase of reaction time, the enzyme activity gradually decreased. It showed that the ReNHase can catalyze the formation of 5-CVAM from adiponitrile with a high efficiency.

The invention claimed is:

1. A novel system based on a new nitrile hydratase for highly efficient catalytic hydration reaction of aliphatic dinitriles, wherein the concentration of a recombinant bacteria with nitrile hydratase derived from a *Rhodococcus erythropohs* CCM2595 is 1-3 g/L, the concentration of aliphatic dinitriles is 20-50 mM/L, and conversion system comprises phosphate buffer saline solution with pH 7-8.

2. The system according to claim 1, wherein preparation steps of the recombinant bacteria with nitrile hydratase are as follows:
  (1) plasmid construction: the gene sequence of nitrile hydratase from the strain *Rhodococcus erythropohs* CCM2595 contains 2596 nucleotides; plasmid pET-24a (+) is used as the expression vector, according to the characteristics of restriction sites of the plasmid, NdeI and Hind III restriction sites are selected to insert the nitrile hydratase gene which is obtained by PCR; after digestion, a DNA fragment is recovered and purified, and inserted a gene fragment for resistance to kanamycin KanR; T7 terminator is transformed into *E. coli* Top 10, recombinant plasmid is obtained, conformed with digestion and named as G0130349-1;
  (2) protein expression verification: the recombinant plasmid obtained in step (1) is transformed into two competent *E. coli* BL21(DE3) and Arctic Expression (DE3) respectively before adding to LB liquid medium for culture and expansion, then the obtained bacterial solution is coated on LB solid plate containing 50 μg/ml kanamycin (kan) before inverted culture at 37° C. for 24 h; monoclone on the plate is selected and planted in LB liquid medium, cultured when OD value reaches 0.6-0.8, then 0.1-1 mM/L Isopropylthiogalactoside (IPTG) is added as inducer for 3-24 h; after the induction, the bacteria are collected by centrifugation; the bacteria are broken by ultrasonic after washing with PBS; SDS-PAGE analysis is carried out to verify the protein expression of nitrile hydratase;
  (3) preparation of bacterial solution: the monoclone picked from Arctic Expression (DE3) plate in step (2) is inoculate to LB liquid medium which contains 50 μg/ml Kan; seed solution is obtained and collected after 37° C. and 220 rpm for 12-18 h of shake cultivation; the seed solution is then inoculated into LB liquid medium containing 50 μg/ml Kan with volume ratio of 1%; when OD value reaches 0.6-0.8 after shake cultivation at 37° C., IPTG is added to reach a final concentration of 0.1 mM/L; after continuous shake cultivation at 16° C. and 220 rpm for 24 h, fermentation broth is collected; the bacteria is collected by centrifugation and washed with pH7-8 PBS buffer for 2-3 times and resuspended for use.

3. The system according to claim 1, wherein, the aliphatic dinitriles comprises adiponitrile, malononitrile, butanedinitrile and sebaconitrile.

* * * * *